US010909498B2

(12) United States Patent
Wicks et al.

(10) Patent No.: US 10,909,498 B2
(45) Date of Patent: *Feb. 2, 2021

(54) MEDICAL CABINET COMMUNICATION SYSTEM AND METHODS

(71) Applicant: Wavemark, Inc., Concord, MA (US)

(72) Inventors: Nathan John Wicks, Clinton, MA (US); Richard Eugene Leitermann, Arlington, MA (US); Jean-claude Jacques Saghbini, Newton, MA (US); Lars Rohrberg, Groton, MA (US)

(73) Assignee: WAVEMARK, INC., Concord, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/848,355

(22) Filed: Apr. 14, 2020

(65) Prior Publication Data

US 2020/0242545 A1     Jul. 30, 2020

Related U.S. Application Data

(63) Continuation of application No. 16/151,080, filed on Oct. 3, 2018, now Pat. No. 10,621,546, which is a
(Continued)

(51) Int. Cl.
| | |
|---|---|
| *G06K 19/00* | (2006.01) |
| *G06Q 10/08* | (2012.01) |
| *A47F 5/00* | (2006.01) |
| *G06F 19/00* | (2018.01) |
| *G06Q 50/22* | (2018.01) |

(Continued)

(52) U.S. Cl.
CPC ......... *G06Q 10/087* (2013.01); *A47F 5/0043* (2013.01); *G06F 19/00* (2013.01); *G06F 19/30* (2013.01); *G06K 7/10297* (2013.01);

*G06Q 50/22* (2013.01); *G16H 20/13* (2018.01); *G16H 50/70* (2018.01); *H04B 5/0062* (2013.01);
(Continued)

(58) Field of Classification Search
CPC ........ G06Q 10/87; G06Q 50/22; G16H 20/13; G16H 50/70; H04W 4/80; A47F 5/0043; A47F 2010/025; G06K 7/10297; H04B 5/0062
USPC ................................................. 235/385, 380
See application file for complete search history.

(56) References Cited

U.S. PATENT DOCUMENTS

| | | |
|---|---|---|
| 4,679,046 A | 7/1987 | Curtis et al. |
| 5,739,765 A | 4/1998 | Stanfield et al. |
| (Continued) | | |

FOREIGN PATENT DOCUMENTS

| | | |
|---|---|---|
| WO | WO 2004/069699 A2 | 8/2004 |
| WO | WO 2007/064816 A2 | 6/2007 |

*Primary Examiner* — Karl D Frech
(74) *Attorney, Agent, or Firm* — Arent Fox LLP

(57) ABSTRACT

Described is an RFID-enabled medical item storage, organization, and/or tracking device, such as a cabinet or shelf, that includes a limited-range wireless network communication capability, such as low-energy Bluetooth or Zigbee, to communicate with nearby cabinets, shelves or mobile devices, any of which may serve as a communication aggregator to coordinate the communication of multiple cabinets, shelves and other devices with an inventory management system or other back-end computer system or other device via back haul wireless or wired networks (e.g., the Internet).

20 Claims, 4 Drawing Sheets

Related U.S. Application Data continuation of application No. 15/455,065, filed on Mar. 9, 2017, now Pat. No. 10,115,073.

(60) Provisional application No. 62/305,887, filed on Mar. 9, 2016.

(51) Int. Cl.
    *H04B 5/00* (2006.01)
    *H04W 4/80* (2018.01)
    *G06K 7/10* (2006.01)
    *G16H 50/70* (2018.01)
    *G16H 20/13* (2018.01)
    *A47F 10/02* (2006.01)

(52) U.S. Cl.
    CPC ......... *H04W 4/80* (2018.02); *A47F 2010/025* (2013.01)

(56) References Cited

U.S. PATENT DOCUMENTS

| | | |
|---|---|---|
| 5,771,003 A | 6/1998 | Seymour |
| 5,774,059 A | 6/1998 | Henry et al. |
| 5,790,409 A | 8/1998 | Fedor et al. |
| 5,848,593 A | 12/1998 | McGrady et al. |
| 5,993,046 A | 11/1999 | McGrady et al. |
| 6,109,774 A | 8/2000 | Holmes et al. |
| 6,151,536 A | 11/2000 | Arnold et al. |
| 6,335,686 B1 | 1/2002 | Goff et al. |
| 6,401,991 B1 | 6/2002 | Eannone |
| 6,445,297 B1 | 9/2002 | Nicholson |
| 6,512,459 B2 | 1/2003 | Benezech et al. |
| 6,563,425 B2 | 5/2003 | Nicholson et al. |
| 6,658,322 B1 | 12/2003 | Frederick et al. |
| 6,677,857 B2 | 1/2004 | Bara et al. |
| 6,703,935 B1 | 3/2004 | Chung et al. |
| 6,707,381 B1 | 3/2004 | Maloney |
| 6,861,993 B2 | 3/2005 | Waldner |
| 6,903,656 B1 | 6/2005 | Lee |
| 6,956,538 B2 | 10/2005 | Moore |
| 6,961,000 B2 | 11/2005 | Chung |
| 6,989,749 B2 | 1/2006 | Mohr |
| 6,989,796 B2 | 1/2006 | Rahim |
| 7,015,815 B1 | 3/2006 | Feibelman |
| 7,142,118 B2 | 11/2006 | Hamilton et al. |
| 7,158,030 B2 | 1/2007 | Chung |
| 7,213,767 B2 | 5/2007 | Tethrake et al. |
| 7,256,699 B2 | 8/2007 | Tethrake et al. |
| 7,258,249 B1 | 8/2007 | Frederick et al. |
| 7,362,228 B2 | 4/2008 | Nycz et al. |
| 7,378,836 B2 | 5/2008 | Teoh et al. |
| 7,394,361 B1 | 7/2008 | Twitchell, Jr. |
| 7,463,947 B1 | 12/2008 | Frederick et al. |
| 7,466,232 B2 | 12/2008 | Neuwirth |
| 7,596,427 B1 | 9/2009 | Frederick et al. |
| 7,689,316 B1 | 3/2010 | Frederick et al. |
| 7,757,947 B2 | 7/2010 | Reznik et al. |
| 8,019,470 B2 | 9/2011 | Meek, Jr. et al. |
| 8,094,028 B2 | 1/2012 | Braun et al. |
| 8,170,714 B2 | 5/2012 | Spano, Jr. et al. |
| 8,195,329 B2 | 6/2012 | Pinney et al. |
| 8,226,414 B2 | 7/2012 | Bodin et al. |
| 8,264,366 B2 | 9/2012 | Chamarti et al. |
| 8,275,665 B2 | 9/2012 | Bodin et al. |
| 8,453,548 B2 | 6/2013 | Jaynes |
| 8,484,049 B2 | 7/2013 | Mullenger et al. |
| 8,485,391 B2 | 7/2013 | Vlastakis et al. |
| 8,521,327 B2 | 8/2013 | Pinney et al. |
| 8,527,090 B2 | 9/2013 | Monto et al. |
| 8,571,701 B2 | 10/2013 | Lunak et al. |
| 8,640,586 B2 | 2/2014 | Jaynes |
| 8,648,699 B2 | 2/2014 | Iasella et al. |
| 8,910,827 B2 | 12/2014 | Lockwood |
| 9,135,482 B2 | 9/2015 | Caputo et al. |
| 9,171,415 B2 | 10/2015 | Adams et al. |
| 9,189,769 B2 | 11/2015 | Caputo et al. |
| 9,224,124 B2 | 12/2015 | Rahim et al. |
| 9,355,220 B2 | 5/2016 | Paydar et al. |
| 9,357,961 B2 | 6/2016 | Arefieg |
| 9,358,334 B2 | 6/2016 | Arefieg |
| 9,399,543 B2 | 7/2016 | Longley et al. |
| 9,418,267 B1 | 8/2016 | Josey |
| 9,443,370 B2 | 9/2016 | Carson et al. |
| 9,526,920 B2 | 12/2016 | Tanis et al. |
| 10,115,073 B2 | 10/2018 | Wicks et al. |
| 2002/0143320 A1 | 10/2002 | Levin |
| 2002/0196126 A1 | 12/2002 | Eisenberg et al. |
| 2003/0030539 A1 | 2/2003 | McGarry et al. |
| 2003/0034390 A1 | 2/2003 | Linton et al. |
| 2003/0117281 A1 | 6/2003 | Sriharto et al. |
| 2003/0160698 A1 | 8/2003 | Andreasson et al. |
| 2003/0164401 A1 | 9/2003 | Andreasson et al. |
| 2003/0174099 A1 | 9/2003 | Bauer et al. |
| 2004/0032328 A1 | 2/2004 | Rubinstein |
| 2004/0046020 A1 | 3/2004 | Andreasson et al. |
| 2004/0098166 A1 | 5/2004 | Spano, Jr. et al. |
| 2004/0133705 A1 | 7/2004 | Broussard et al. |
| 2004/0140884 A1 | 7/2004 | Gallagher, III et al. |
| 2004/0158507 A1 | 8/2004 | Meek, Jr. et al. |
| 2005/0006569 A1 | 1/2005 | Yoshiyuki |
| 2005/0016303 A1 | 1/2005 | Jacobs et al. |
| 2005/0189370 A1 | 9/2005 | Carter et al. |
| 2006/0122858 A1 | 6/2006 | Miles et al. |
| 2006/0272976 A1 | 12/2006 | Pinney et al. |
| 2007/0001809 A1 | 1/2007 | Kodukula et al. |
| 2007/0229268 A1 | 10/2007 | Swan et al. |
| 2008/0256998 A1 | 10/2008 | Mallian et al. |
| 2008/0275586 A1 | 11/2008 | Ko et al. |
| 2011/0202170 A1 | 8/2011 | Dawes et al. |
| 2011/0295198 A1 | 12/2011 | Buisson |
| 2013/0076215 A1 | 3/2013 | Davidowitz et al. |
| 2015/0278461 A1 | 10/2015 | Danilewitz |
| 2017/0076361 A1* | 3/2017 | Levesque ........... G06Q 30/0639 |

\* cited by examiner

MEDICAL CABINET COMMUNICATION SYSTEM AND METHODS

CROSS-REFERENCE TO RELATED APPLICATIONS

This application is a continuation of U.S. patent application Ser. No. 16/151,080, filed Oct. 3, 2018, issued as U.S. Pat. No. 10,621,546, which claims priority to and the benefit of U.S. patent application Ser. No. 15/455,065, filed Mar. 9, 2017, issued as U.S. Pat. No. 10,115,073, which claims priority to and the benefit of U.S. Provisional Patent Application No. 62/305,887, filed Mar. 9, 2016, entitled "MEDICAL CABINET COMMUNICATION SYSTEM AND METHODS", the entirety of the contents of each of the preceding applications is incorporated herein by reference, as if fully set forth in this document, for all purposes.

BACKGROUND

Field of the Technology

The present disclosure describes an RFID-enabled medical item storage, organization, and/or tracking device, such as a cabinet or shelf, that includes a limited-range wireless network communication capability, such as low-energy Bluetooth or Zigbee, to communicate with nearby cabinets, shelves or mobile devices, any of which may serve as a communication aggregator to coordinate the communication of multiple cabinets, shelves and other devices with an inventory management system or other back-end computer system or other device via back haul wireless or wired networks (e.g., the Internet).

Background of the Technology

Radio Frequency Identification (RFID) systems have been used to track medical item supplies in hospitals and through the medical item supply chain. Such systems typically involve one or more readers and many RFID tags, each of which is associated with (e.g., attached to) items being monitored or tracked. In the case of pharmaceuticals, single-use medical devices, and implantable medical devices, RFID tags are typically affixed to or made part of the item's packaging or container. An advantage of RFID tags is that they are stand-off readable (i.e., readable at a distance without a requirement for contact or a direct line of sight path between the reader and the tag).

RFID tags take the form of integrated circuits, with associated antennas, that have computer readable memory encoded with unique serial numbers. RFID tags typically can be encoded with other information in addition to unique serial numbers either at the time of manufacture or thereafter by writing data to a writeable or re-writable computer readable memory of the RFID tag. The reader includes or is connected to an antenna used to generate a carrier signal that energizes the RFID tag antenna when the RFID tag is within the electromagnetic field generated by the reader's antenna. The energized RFID tag generates a data signal that is transmitted by the tag's antenna and received by the RFID reader's antenna. The reader and/or its associated antenna can be in a fixed location or may be mobile, such as carried by an operator. For example, RFID readers are often placed at multiple, distributed locations associated within a supply chain in order to monitor the items as they pass through manufacturing, transportation, distribution, storage, to consumption. Each reader captures the RFID tag serial numbers of each item as it enters the reader's interrogation field, and data collected from all readers facilitates item tracking over time, through and within the supply chain.

Medical item cabinets may be equipped with one or more RFID readers to interrogate and read the contents of the RFID tags associated with the items stored in or near the cabinet to monitor or track the tagged items. Such cabinets typically include a computer (i.e., central processing unit (CPU)) that processes and/or stores information read from the RFID tags and serves as the communication hub for the cabinet. These cabinets are typically connected via a primary communication channel to the Internet or other communications network (i.e., the "cloud") using a wired or Wi-Fi network adapter connected to the cabinet's computer. This primary communication channel is used to communicate information between the cabinet and remotely located servers or other computer systems, such as an inventory management system, for several purposes, including to:

(1) send information read from medical item tags (i.e., bar code or RFID tags) from the cabinet to the cloud during or after a cabinet inventory read cycle;
(2) modify cabinet settings, such as the frequency of inventory read cycles;
(3) update software or firmware on the cabinet remotely; and
(4) send diagnostic commands to assess problems and obtain diagnostic information and logs.

From time-to-time, a problem may occur in which the symptom is a communication failure between the cabinet and the remote servers. This can happen due to several possible reasons, including:

(i) the cabinet's computer or network adapter has failed;
(ii) the cabinet has lost power (e.g., the cabinet has been unplugged from a wall outlet); or
(iii) the cabinet has been disconnected from the network by, for example, a wired communication cable has been unplugged, the cabinet has moved out of range of a wireless network, or unintended changes have been made to the settings of the hospital network or the cabinet's computer or network adapter.

When a cabinet fails to communicate with the cloud, remote tracking of the medical items stored by the cabinet is delayed at least until communication can be reestablished. On occasion it is necessary for a service technician to travel to the location of the cabinet to diagnose and resolve the issue, which can cause significant delay and associated costs. Furthermore, this gap in communication can result in inventory shortages and increased risk of inventory loss due to diversion or theft. It is desirable to reduce the frequency and duration of communication failures between medical item storage cabinets and the cloud in order to provide more accurate and timely remote inventory monitoring and tracking.

SUMMARY

Certain aspects of the present disclosure include equipping a medical item storage cabinet or individual shelves of such storage cabinet with a limited-range wireless network capability that allows a remote determination of, for example, whether the cabinet (or shelf) has power, that its computer or RFID reader is functioning properly, and perhaps that a simple call to the hospital IT department is warranted to perform repair and re-connection. In certain aspects, a first medical item storage cabinet is configured to communicate through (i) a primary communication channel with a remotely located inventory management system; and (ii) a secondary communication channel with a nearby cabinet via a short-range wireless network channel. In certain aspects, the nearby cabinet may relay communications received from the first cabinet to the inventory management system via the nearby cabinet's primary communication channel or via the nearby cabinet's secondary communication channel to another nearby cabinet. In certain other aspects, the nearby cabinet may process information received from the first cabinet via the secondary communication channel and transmit information to the inventory management system based on the information received from the first cabinet.

In certain aspects, the first cabinet includes a transceiver device that broadcasts a short-range wireless network signal. The signal may be received by a nearby cabinet, shelf, or mobile device and may include information about the first cabinet such as, for example, an operational status of the cabinet. In certain aspects, the signal includes information about the medical items stored in or near the cabinet. For example, the signal may include serial numbers of the tags associated with the stored medical items, additional information about the stored medical items such as, for example, expiration dates, and/or the signal may include notification information such as, for example, information indicating that one or more of the stored medical items has expired.

In certain aspects, the first cabinet includes a two-way transceiver that establishes and transmits and/or receives signals via the secondary communication channel. The first cabinet may communicate via the secondary communication channel with a nearby cabinet, shelf, or mobile device. The first cabinet may transmit information via the secondary communication channel such as, for example, information about the operational status of the first cabinet or of nearby cabinets, information containing instructions or commands such as, for example, information instructing a nearby cabinet or mobile device to change the settings of its network adapter, serial numbers of the tags associated with the medical items stored in or near the first cabinet or nearby cabinets, additional information about the stored medical items such as, for example, expiration dates, and/or notification information such as information indicating that one or more of the stored medical items has expired. The first cabinet may receive information via the secondary communication channel from nearby cabinets or nearby mobile devices. The received information may include, for example, information about the operational status of nearby cabinets or mobile devices, information containing instructions or commands such as, for example, information instructing the first cabinet to restart or change the settings of its network adapter, and/or information associated with the medical items stored by the first cabinet or nearby cabinets such as, for example, expiration dates.

Certain aspects of the present disclosure are directed to a system for tracking within a facility medical items having associated RFID tags, the system including a plurality of medical item supply locations that store the medical items, and a handheld RFID reader that reads the RFID tags associated with the medical items. The medical supply locations may broadcast a signal via a short-range wireless network protocol. The RFID reader may determine a strength of the short-range wireless network signals, and based on the determination, the RFID reader may display a selectable list of the medical supply locations. The selectable list may be filtered to display only the medical supply locations that have a threshold strength of the short-range wireless network signal or that are computed to be less than a threshold distance away from the RFID reader. The RFID reader may enable entry of a transaction or inventory count associated only with the medical supply locations included in the selectable list.

BRIEF DESCRIPTION OF THE DRAWINGS

The disclosed embodiments will hereinafter be described in conjunction with the appended drawings, provided to illustrate and not to limit the disclosed aspects, wherein like designations denote like elements, and in which.

DETAILED DESCRIPTION

Various aspects are now described with reference to the drawings. In the following description, for purposes of explanation, numerous specific details are set forth in order to provide a thorough understanding of one or more aspects. It may be evident, however, that such aspects may be practiced without these specific details.

Figure 1:
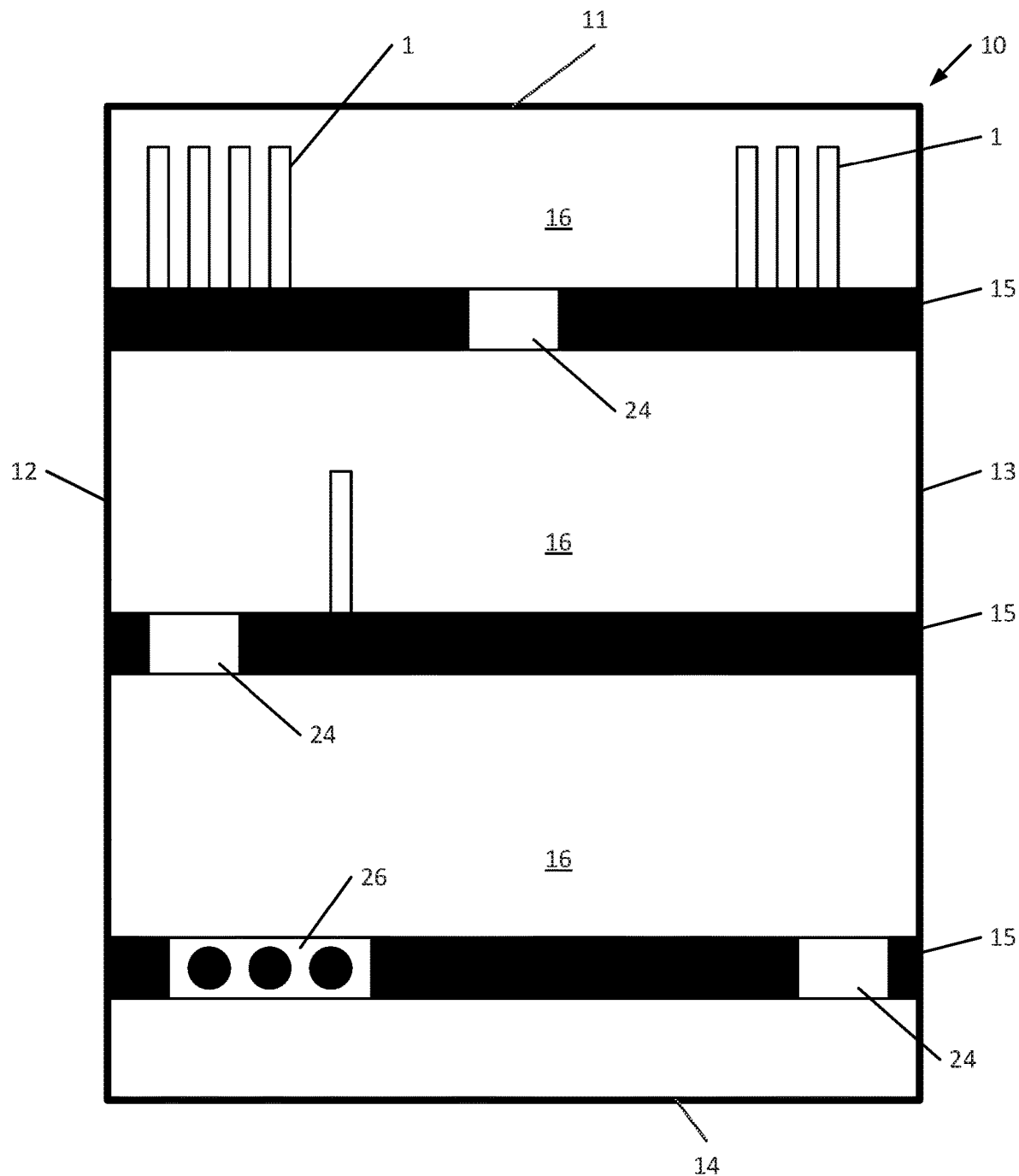
FIG. 1 is a front schematic view of an RFID cabinet storage device for holding medical items in accordance with certain aspects of the present disclosure.

A hospital or other medical care facility generally includes multiple medical supply storage rooms devoted to housing supplies including medical items, and procedure rooms where the medical items are used, such as consumed during medical procedures or implanted in patients. These supply rooms may include a number of medical item cabinet storage devices that store the medical items in proximity to the procedure rooms until they are used. FIG. 1 illustrates one embodiment of a cabinet storage device ("cabinet") 10 in accordance with the present disclosure. The cabinet 10 may store rows of items, such as medical items 1, which may include implanted devices (e.g., cardiac stents and joint replacements), disposables (e.g., catheters and hypodermic syringes), and equipment (e.g., imaging and monitoring devices), for example.

In the embodiment of FIG. 1, the cabinet 10 has a top wall 11, a left side wall 12, a right 13 side wall, and a bottom wall 14, together defining an interior space. At least one shelf 15 separates the cabinet's interior space into distinct storage regions 16. In an exemplary embodiment, at least one of the cabinets 10 in a storage room is a radio frequency identification (RFID) equipped cabinet 10 that includes an associated RFID reader 20 (FIG. 2) that can detect and read information embedded in RFID tags associated with (e.g., attached to) the medical items 1 stored within the cabinet 10. In this disclosure, the term "shelf" refers to a generally planar member capable of supporting an object, and the term "cabinet" refers to a structure including one or more shelves. These terms, however, are not intended to be limiting as to the physical attributes of any structure that may be used to implement embodiments of the present disclosure, but are used merely for convenience in explaining certain embodiments. Any known structure for storing, housing, or otherwise supporting an object may be used in implementing the various embodiments of this disclosure.

Figure 2:
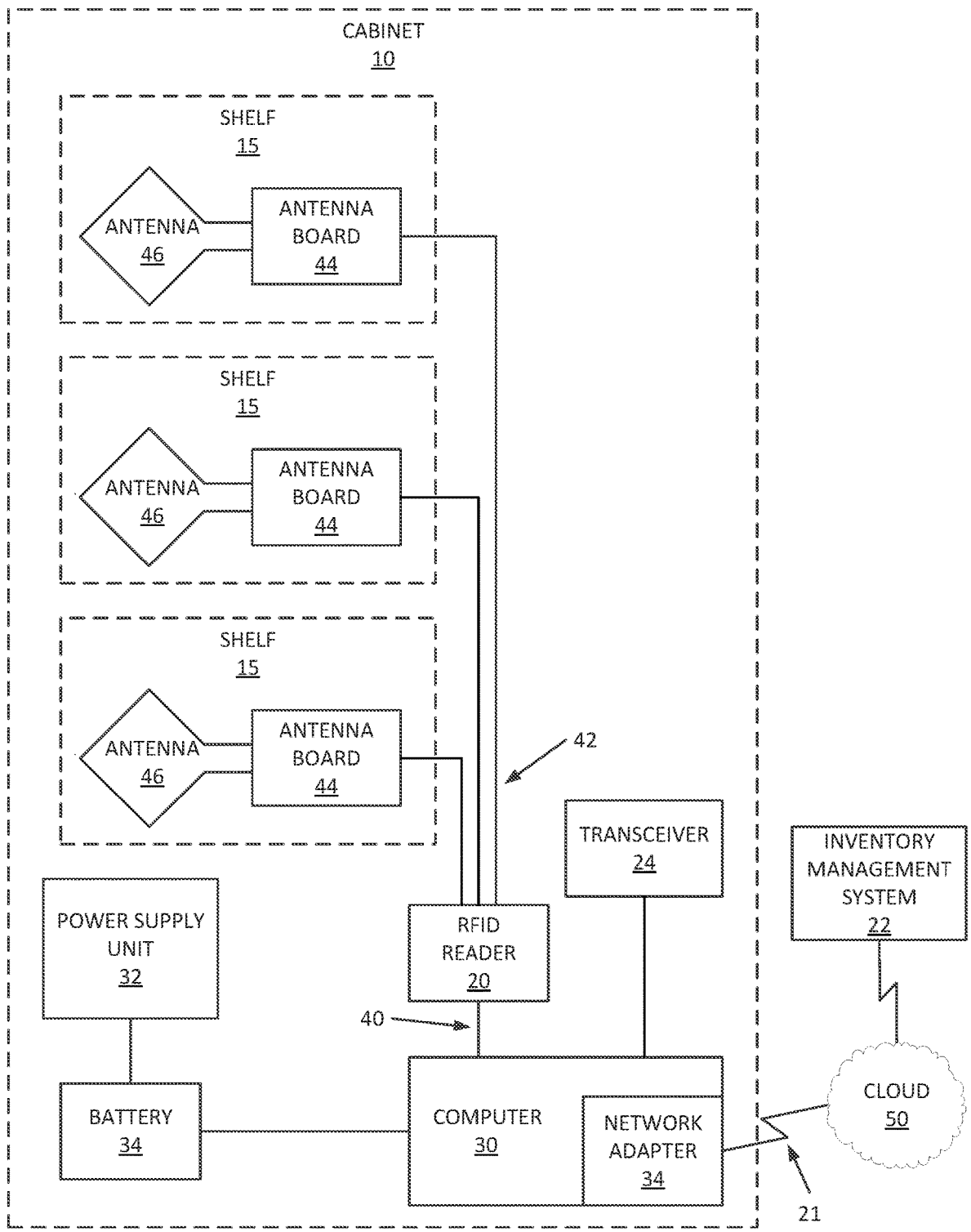
FIG. 2 is a block diagram of a medical item storage cabinet system in accordance with certain aspects of the present disclosure.
Figure 3:
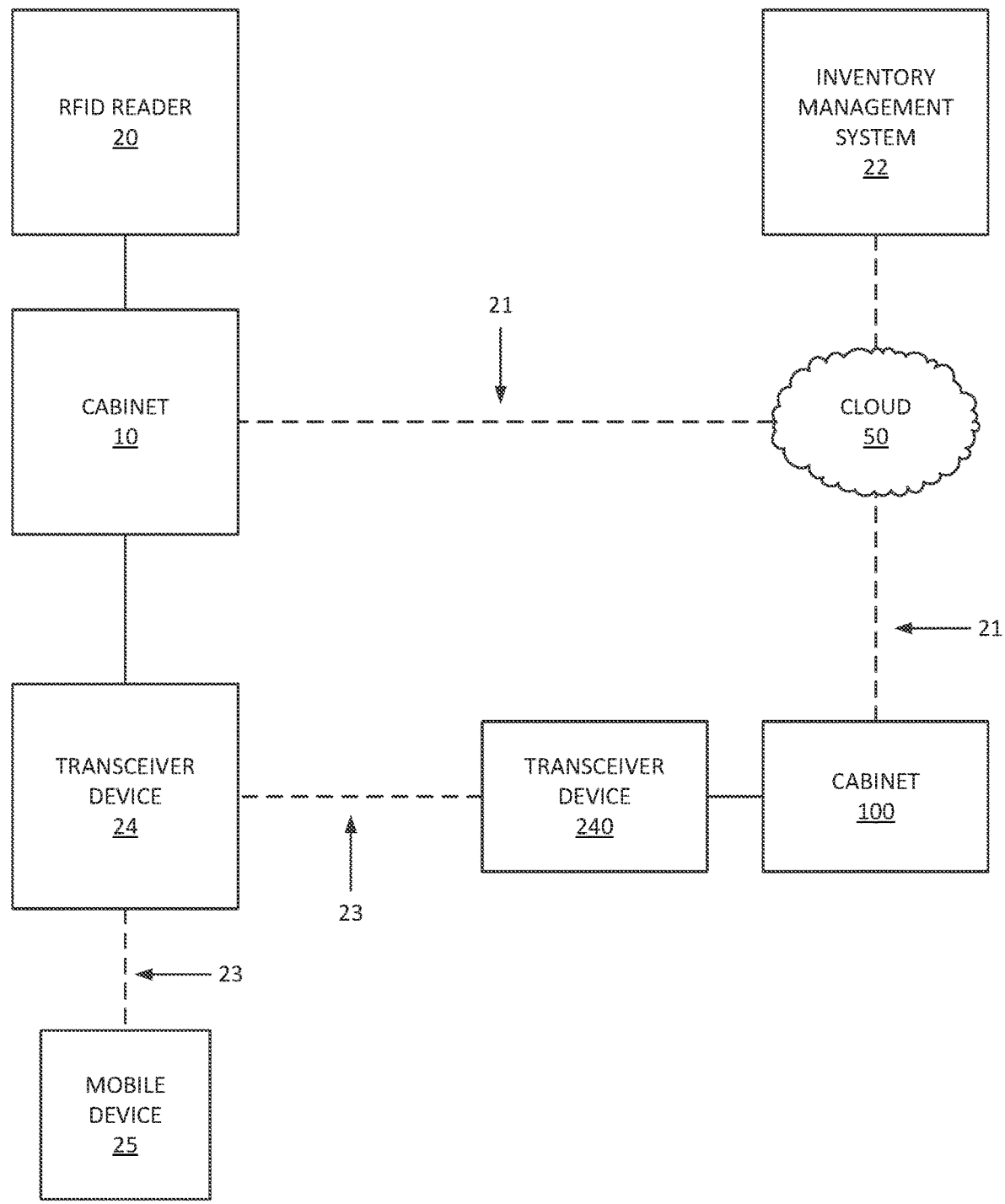
FIG. 3 is a block diagram of a medical item storage cabinet communication system in accordance with certain aspects of the present disclosure.

One embodiment of a storage cabinet system in accordance with this disclosure is illustrated in FIGS. 2 and 3. In this embodiment, the cabinet 10 includes a power supply unit (PSU) 32 that supplies power from an external source, such as a standard power outlet, to the cabinet's computer 30 and to other electrical components (e.g., RFID reader 20) by direct power cable connections and/or indirectly through connections with one or more of the other components as illustrated in FIG. 2. Optionally, the cabinet 10 may include a backup power supply, such as a battery 34 that supplies power to one or more electrical components in the event of a main power failure (e.g., the cabinet is unplugged from the external power source or the PSU 32 fails). The computer 30 is connected to the RFID reader 20 through a digital signal connection 40. The RFID reader 20 is connected via RF signal connections 42 to antenna boards 44 and their associated antennas 46 located in each shelf 15.

The computer 30 is connected to a primary communication network via network adapter 34. Specifically, as illustrated in FIGS. 2 and 3, the computer 30 communicates with an inventory management system 22 via a primary communication channel 21, such as a wired local area network (LAN) or a wireless Wi-Fi network that is connected to the inventory management system 22 via "the cloud" 50, which can include any communication link or network, for example, the Internet, Ethernet, a local network, Controller Area Network (CAN), serial, Local Area Network (LAN), or Wide Area Network (WAN). The inventory management system 22 may then be used to track the presence of the medical items 1 in the cabinet 10 in real-time without intervention by staff. Thus, there is no action required by the hospital personnel in order to enable the inventory management system 22 to detect the presence of the medical items 1. Further, there is no staff intervention required when items 1 are removed since periodic scans of the cabinet's entire contents by the reader 20 detects removal, which is determined by or reported to the inventory management system 22.

An RFID reader in accordance with this disclosure includes any device capable of receiving RF signals transmitted by the RFID tags and converting the received RF signals to digital signals. For example, in various embodiments, the RFID reader may include or be connected to one or more antennas, with associated antenna boards. The antenna boards may not be needed for some designs. If present, antenna boards may include tuning components (e.g., tuning circuitry) and other components (e.g., LED indicators) and may include logic and switching controls as necessary to perform the operations described herein. In various embodiments, the antenna boards include signal processors that convert the RF signals received by the antennas to digital signals, and digital signals received, for example, from the computer into RF signals to be transmitted by the antennas. In some embodiments, the RFID readers include communication adapters capable of communicating the digital signals to the cabinet's computer or directly to the inventory management system via the cloud. In other embodiments, the antenna boards are connected via RF signal cables to the cabinet's computer or to a separate signal processing unit in communication with the computer.

Accordingly, the term "computer" may refer to a device that is separate from, but in communication with, one or more RFID readers, or it may refer to one or more RFID readers that include the communication circuitry or other components capable of communicating information received from the RFID tags to the inventory management system. In various embodiments, the computer may include a processing device (e.g., microprocessor, discrete logic circuit, application specific integrated circuit (ASIC), programmable logic circuit, digital signal processor (DSP), etc.) and other associated hardware as may be necessary to process, store, and communicate information, as well as connect to and operate with the cabinet's various electrical components described herein.

For simplicity, the terms "cabinet" and "shelf" may be used generally to refer to equipment that may include associated computers, RFID readers, antennae, and other components. For example, if it is described that "a cabinet reads RFID tags," it should be understood that the RFID tags are read by one or more RFID readers associated with the cabinet, and if it is described that "a cabinet communicates with the inventory management system," it should be understood that the cabinet's computer or RFID reader communicates with the inventory management system through the primary communication channel via the network adapter connected to the computer or RFID reader, or through the secondary communication channel via the transceiver as described in greater detail below.

In one preferred embodiment, the term "RF signal" refers to radio frequency signals used, for example, to interrogate an RFID reader antenna or group of antennae. However, it is understood that the term "RF signal" also refers to any other signals capable of being used with the exemplary devices, systems, and methods including, but not limited to, DC pulse communications, or voltage-level based communications (TTL, etc.). The term "digital signal" refers, in one preferred embodiment, to any binary signal encoding data that can be transported via any suitable carrier (e.g., CAN bus, RS-232, RS-485 serial protocols, Ethernet protocols, Token Ring networking protocols, etc.).

Referring again to FIGS. 2 and 3, the cabinet 10 includes a transceiver device 24 configured to communicate via a secondary communication channel 23, namely a short-range wireless network channel (such as Bluetooth, Bluetooth low-energy (BTLE), near-field communication (NFC) or Zigbee). In this exemplary embodiment, as illustrated in FIG. 3, at least two of the cabinets 10, 100 are located near each other in a medical supply storage room or a procedure room (or separate rooms near to each other) and each cabinet 10, 100 is equipped with a transceiver device 24, 240 capable of communicating via the secondary communication channel 23. If the two cabinets 10, 100 are in communication via the secondary channel 23, communication between the cabinet 10 and the inventory management system 22 can be re-established in a scenario where the primary communication channel 21 is unavailable, such as when the cabinet 10 has been disconnected from a wired network by unplugging a cable, by the cabinet moving out of range of a wireless network, or by unintended changes to the settings of a facility's network.

Each transceiver 24, 240 may be capable of one-way or two-way communication. A BTLE radio (not shown) included in transceiver 24, 240, for example, may include a transmitter and a receiver. The BTLE radio can be instructed to act as a one-way communication device for a period of time. In that case, the BTLE radio only transmits a signal (i.e., "beacon"). For example, the inventory management system 22 may instruct the transceiver 24, 240 to transmit a one-way beacon signal indicating that a product stored on the associated cabinet has expired or been recalled. A handheld mobile device 25 may be configured to receive the beacon signal and notify the user that the cabinet contains the expired or recalled product. Alternatively, the BTLE radio can be instructed to become a two-way communication device, and "pair" with a particular nearby shelf or cabinet. Once that is done, a two-way communication link is established. In exemplary embodiments, cabinets 10, 100 that are considered sufficiently near to be paired with each other may be located up to substantially 30-100 feet apart.

If two nearby cabinets 10, 100 can communicate through the secondary channel 23, valuable information about the cabinet 10 can be obtained remotely even if the cabinet's primary communication channel is offline. For example, if the offline cabinet 10 determines that it is plugged-in, turned-on, and its computer is working, but the facility (i.e., hospital) network is either unplugged or otherwise not functioning for that cabinet 10, then the offline cabinet 10 can transmit a signal via the secondary channel 23 indicating such status. In this scenario, an adjacent cabinet 100 could then receive the transmitted signal from the transceiver 24 of the offline cabinet 10 and communicate the status of the offline cabinet 10 to the inventory management system 22. In various embodiments, the nearby cabinet 100 can digitally pair itself to (i.e., establish a two-way communication link with) the offline cabinet 10 and exchange messages with the offline cabinet 10 via the secondary channel 23. These messages can include additional diagnostic information about the offline cabinet 10, information read from the RFID tags stored in or near the offline cabinet 10, or instructions to be executed by the offline cabinet 10, such as instructions to reset or change its network settings.

Furthermore, the cabinet 10 may be equipped with a battery backup power source 34 so that the cabinet 10 can operate and/or communicate via the secondary channel 23 even if the primary power supply to the cabinet 10 is disconnected. If the transceiver 24 of the offline cabinet 10 has backup power available from the battery 34, it can transmit a beacon signal or pair itself to and exchange messages with a transceiver 240 of a nearby cabinet 100. The signal or message can include diagnostic or status information, for example that it (the offline cabinet 10) is running on backup power and needs to be plugged-in. The messages may also include information that the cabinet 10 would otherwise transmit via the primary communication channel 21 during normal operation, such as inventory counts or other information read from the RFID tags stored in or near the cabinet. Thus, through this additional secondary communication channel 23, valuable information can be obtained from, and delivered to, the offline cabinet 10 through the communication link established with the nearby cabinet 100 without requiring a technician to perform a visit to physically inspect the offline cabinet 10, which can be expensive and time consuming. Additionally, operating data such as inventory counts can be transmitted to the inventory management system 22 with little or no delay or interruption.

Figure 4:
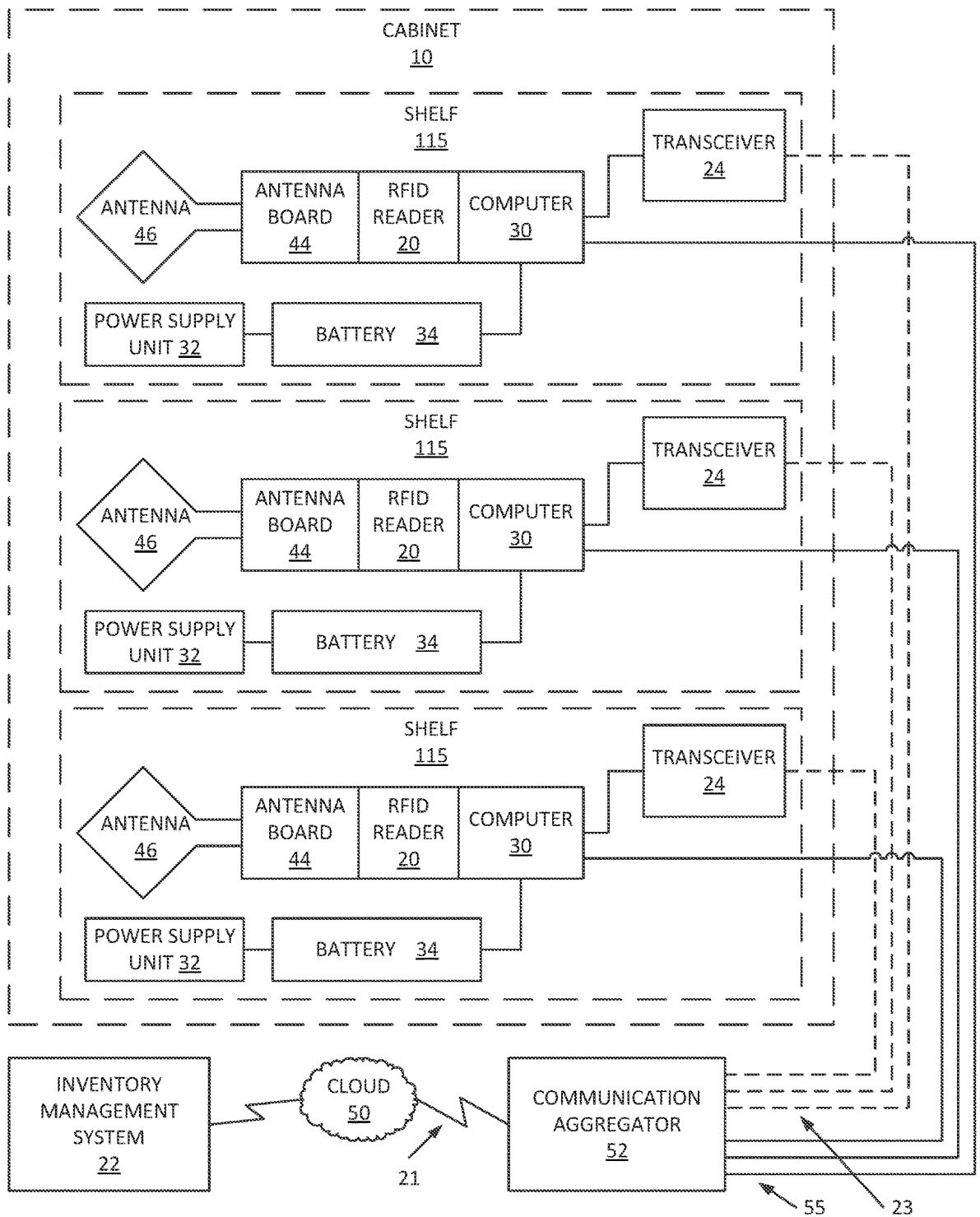
FIG. 4 is a block diagram of a medical item storage cabinet system in accordance with certain other aspects of the present disclosure.

In various embodiments, the transceiver 24 is used to communicate through the secondary channel 23 with a mobile device 25, such as a handheld RFID reader, a computer tablet or a cellular phone. The short-range wireless transceiver 24 may be located on or in a cabinet 10 as illustrated in FIG. 2, and/or it may be located on or in one or more shelves 15, 115 as illustrated in FIGS. 1 and 4. Although the transceiver 24 may be located anywhere on the shelf 15, it may be advantageous to position the transceiver 24 at a level on the shelf 15 where the transceiver 24 will be as close as possible to a mobile device 25 carried by a staff member, so that the signal strength between the mobile device 25 and the shelf 15 that the staff member seeks to communicate with is as strong as possible compared to other shelves in the room or area. This facilitates a determination of which transceiver(s) 24 the mobile device 25 pairs with. Once the transceiver 24 establishes a connection with the mobile device 25, the system 22 may cause the shelf 15 to display a visual signal (such as a flashing light, LED, etc.) 26 to identify itself to the staff member. Thus, in some embodiments, the transceiver 24 and/or the visual signal display 26 may be positioned at or near the front and center of the shelf 15 so that the staff member can more easily discern proximity to the desired shelf 15. This configuration is illustrated in the upper-most shelf in FIG. 1. Locating the transceiver 24 at or near the front and center of the shelf may not always be possible, and in these cases, the transceiver 24 may be located in other areas, such as on the rear or sides of the shelf (shown in the middle and lower shelves in FIG. 1).

As discussed above and shown on the lower shelf in FIG. 1, a shelf 15 may be equipped with a light source 26 (such as a LED) that emits light in multiple colors, indicating various status levels. For example, LED lights 26 on a shelf 15 may emit green, yellow, or red light. If the shelf 15 emits a green light, this may indicate that all is well with the shelf 15. If the shelf 15 emits a yellow light, this may indicate that there is one or more non-critical alerts available about the state of that shelf 15. Examples of non-critical alerts include that stock of a particular medical item 1 is below-par or above-par for items normally stocked on that shelf 15. If the shelf 15 emits a red light, this may indicate that there are critical alerts, possibly safety related, for that shelf 15. Examples of critical alerts include that an expired or recalled medical item is on that shelf 15, or that the shelf is not in communication with the inventory management system 22. It is to be understood by those skilled in the art that any combination of colors may be used to indicate status of the shelf 15. In addition to flashing a color, the lights 26 may also blink, or shine brighter or dimmer to indicate the urgency of the alert. Audible signals emitted in various intervals or tones may also be used to indicate alerts.

In some embodiments, the shelf 15 connects with the cabinet 100, which contains the necessary hardware (i.e., computer and/or RFID reader) to read and/or process the RF or digital signals and communicate with the inventory management system 22. In various other embodiments, the shelf can be configured as a "smart shelf" such that it can operate independent of a cabinet 100. For example, as illustrated in FIG. 4, a smart shelf 115 may include its own RFID antenna 46, RFID reader 20, computer 30, network adapter 34, and/or transceiver 24 such that the shelf 115 can read RFID tags and communicate with the inventory management system 22 and/or with other nearby shelves or cabinets via its transceiver 24 independent of another cabinet or shelf. In these embodiments, for example, the smart shelf 115 could be placed onto a table or used to retrofit an existing shelf in a cabinet.

It will be appreciated by those skilled in the art that in some embodiments, a shelf or cabinet may be equipped with a minimal number of electrical components necessary to read and transmit the serial numbers of stored RFID tags (and perhaps a serial number of the shelf or cabinet) to the inventory management system. The inventory management system, based on the received serial numbers, may track the location of the medical items, determine inventory levels on-hand at various locations, and process and analyze additional information that the inventory management system has associated with the serial numbers of the stored medical items, such as product descriptions, lot numbers, and expiration dates. The inventory management system can host and distribute such information to client terminals and mobile devices that may access the inventory management system via the cloud. Additionally, the inventory management system, based on the additional information it processes, may issue certain notifications or instructions to a cabinet or shelf. For example, if the inventory management system determines that a product stored on a particular shelf has expired, the inventory management system may instruct the shelf to display a visual notification (such as illuminate an LED light) or transmit a beacon signal via the shelf's transceiver to indicate that a product on that shelf has expired.

In various other embodiments, in addition to reading and transmitting RFID tag serial numbers, a shelf or a cabinet may be configured to store and/or process additional information independent of the inventory management system. For example, a smart shelf may read additional information encoded on RFID tags, such as a medical item's product description, lot number, and expiration date, or the smart shelf may store a database of such information locally in a computer readable medium. The smart shelf may process and store the additional information, which may then be accessed for example, by a mobile device communicating with the smart shelf via the shelf's transceiver. This arrangement advantageously makes inventory information available at the storage location without the need for a client terminal or mobile device to communicate directly with the inventory management system. For example, such a smart shelf can independently determine whether any of the medical items stored on the shelf have expired, and can transmit a beacon signal alert, display a visual signal, or otherwise make the information available on-site without the need to communicate with the inventory management system.

In the example embodiment of FIG. 4, each shelf 115 may include local intelligence and communicate over a wired bus 55 to a communication aggregator 52 connected to the cloud 50. The aggregator 52 manages the communication of many shelves 115 and may be located in one or more cabinets or shelves, or may be housed independently of any cabinet or shelf as is illustrated in FIG. 4. A shelf 115 can use the wired bus 55 much like a conventional communication channel to communicate to the aggregator 52 in several ways, including:

(1) send information read from medical item tags (i.e., bar code or RFID tags) from the cabinet to the cloud during or after a cabinet inventory read cycle;
(2) modify cabinet settings, such as the frequency of inventory read cycles;
(3) update software or firmware on the cabinet remotely; and
(4) send diagnostic commands to assess problems and obtain diagnostic information and logs.

From time-to-time, a problem can occur in which the symptom is that the shelf 115 loses communication with the wired aggregator 52. If the shelf has access to an alternate short-range wireless network (such as Bluetooth, Bluetooth low-energy (BTLE), or Zigbee), communication can be re-established over this wireless network 23. The shelf 115 would then be able to respond to diagnostic commands and problems can be assessed.

Further, the alternate short-range wireless network 23 can perform additional functions. Currently, when hospital staff interacts with an inventory management system 22 and/or RFID cabinets 10, it is useful to know which shelves 15 or cabinets 10 are in close physical proximity to the staff member. The staff member may be searching for a particular cabinet 10 or shelf 15 carrying a medical item required for a procedure, or the staff member may be searching for expired inventory to be removed from the shelves 15. If the staff member carries a Bluetooth-equipped mobile device 25, such as a handheld RFID reader, a smartphone or a tablet, such device may discern which shelves 15 are nearby by assessing the strength of the signals emitted by the transceivers 24 of the cabinets 10 or shelves 15.

This information might be used to simplify the interaction between the staff member and the inventory that he/she is faced with. When a medical device storage room is initially set up with multiple cabinets 10, shelves 15 and possibly aggregators 52, the setup process can include creation of a digital "map" showing relative physical locations (2D or 3D) of all possible stocking locations and components in the room. Each of these locations can then be mapped to a particular wireless beacon signal 23. Then, when the staff member searches for a particular item 1 known by the inventory management system 22 to be located on a particular shelf 15, software associated with the cabinet 10 and/or the inventory system 22 alerts the staff member whether the correct shelf 15 is nearby, not nearby, forwards, backwards up, down, to the right, to the left, or in an adjacent room. This alerting can be based at least in part on the strength of the signal 23 emitted by the transceiver 24 and recognized by the mobile device 25 carried by the staff member.

Also, some inventory management tasks, such as performing an inventory count, require the staff member to input the physical location or ID number of the cabinet 10/shelf 15. With the short-range wireless signal 23 present, software on the staff member's mobile device 25 may display a drop-down list of possible cabinets 10 populated only by those cabinets 10 that are within a given, relatively close distance of the staff member based on the beacon signals 23 detected by the mobile device 25, for example, within ten feet. This shortens the list of potential cabinets 10 the staff member must choose from, simplifies the inputting process for the staff member, and reduces the possibility of the staff member entering an erroneous cabinet 10. Further, if an erroneous location or cabinet 10 is inputted, the system recognizes that the inputted entry is not nearby and prompts the staff member to correct the mistake.

Additionally, if the staff member is searching for a particular medical device 1 in the inventory, time may be critical to obtain a good medical outcome for a patient. Therefore, in some embodiments, the communication channel between an inventory shelf 15 and a Bluetooth-equipped mobile device 25 may be used to signal the shelf 15 to activate a light 26 or sound to quickly alert the staff member of the shelf's location in real-time.

In another embodiment, a staff member carrying, for example, a Bluetooth-enabled mobile device 25 may enter a room having medical supply cabinets 10 equipped with shelves 15 having status indicator lights 26. The staff member may look around for critical alert lights (i.e., red) and approach that particular shelf 15. Proximity to the beacon signal 23 will inform the mobile device 25 that the staff member is in a position to address the alerts on the particular shelf 15. These alerts are then presented on the mobile device 25 either 1) through the Wi-Fi network 21 or 2) directly from the shelf 10 to the mobile device 25 through a short range wireless network link 23 between the transceiver 24 on the shelf 15 and the mobile device 25.

While the foregoing disclosure discusses example embodiments, it should be noted that various changes and modifications could be made herein without departing from the scope of the described embodiments as defined by the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiment, unless stated otherwise.

We claim:

1. A storage cabinet, comprising:
   a shelf configured to read a radio-frequency identification ("RFID") tag affixed to an item located on the shelf; and
   a communication device configured to communicate with an inventory management system via a communication channel;
   wherein the communication device communicates an inventory signal to the inventory management system comprising information regarding the RFID tag affixed to the item, and
   wherein the inventory management system communicates an action signal to the storage cabinet based on the inventory signal.

2. The storage cabinet of claim 1, wherein the information regarding the RFID tag comprises a unique serial number.

3. The storage cabinet of claim 1, wherein the information regarding the RFID tag comprises a location of the item.

4. The storage cabinet of claim 3, wherein light emitting diodes ("LEDs") are configured to be illuminated based upon the action signal.

5. The storage cabinet of claim 3, wherein LEDs are located on the shelf and are configured to illuminate the location of the item on the shelf.

6. The storage cabinet of claim 1, wherein the inventory management system determines an inventory level of the item based on the inventory signal.

7. The storage cabinet of claim 6, wherein the action signal indicates the inventory level of the item is below a threshold.

8. The storage cabinet of claim 7, wherein the shelf comprises LEDs and are configured to illuminate a color based on the action signal.

9. The storage cabinet of claim 7, wherein the storage cabinet is configured to emit an audible signal based the action signal.

10. The storage cabinet of claim 9, wherein the audible signal is emitted at various intervals or tones.

11. The storage cabinet of claim 1, wherein the shelf comprises a RFID reader.

12. The storage cabinet of claim 1, wherein the inventory management system is located at a cloud server.

13. A method of managing inventory in a storage cabinet, comprising:
   reading a radio-frequency identification ("RFID") tag affixed to an item located on a shelf; and
   communicating with an inventory management system via a communication channel;
   wherein a communication device communicates an inventory signal to the inventory management system comprising information regarding the RFID tag affixed to the item, and
   wherein the inventory management system communicates an action signal to the storage cabinet based on the inventory signal.

14. The method of claim 13, further comprising determining an inventory level of the item based on the inventory signal.

15. The method of claim 14, wherein the action signal indicates the inventory level of the item is below a threshold.

16. The method of claim 15, further comprising illuminating LEDs located on the shelf based on the action signal.

17. The method of claim 16, wherein the LEDs are configured to illuminate with different colors based on the determined inventory level.

18. The method of claim 14, further comprising emitting an audible signal based on the action signal.

19. The method of claim 14, wherein the inventory level is determined based upon a serial number of the RFID tag.

20. The method of claim 13, wherein reading the RFID tag occurs at iterative intervals.

* * * * *